United States Patent [19]
Klearman

[11] Patent Number: 5,478,311
[45] Date of Patent: Dec. 26, 1995

[54] HAND HELD COMBINATION PILL CRUSHING AND DISPENSING DEVICE

[76] Inventor: Jeffrey D. Klearman, #2 Frontenac Pl., St. Louis, Mo. 63131

[21] Appl. No.: 264,480

[22] Filed: Jun. 23, 1994

Related U.S. Application Data

[63] Continuation-in-part of Ser. No. 168,019, Dec. 15, 1993, Pat. No. 5,376,072.
[51] Int. Cl.⁶ ................................................... A61M 37/00
[52] U.S. Cl. ............................. 604/82; 604/218; 604/92; 604/56
[58] Field of Search .......................... 604/56–57, 77–79, 604/92, 82–85, 187, 191, 211, 222, 218, 224, 225

[56] References Cited

U.S. PATENT DOCUMENTS

| | | |
|---|---|---|
| 1,165,686 | 12/1915 | McElroy . |
| 4,057,052 | 11/1977 | Kaufman et al. . |
| 4,568,331 | 2/1986 | Fischer et al. . |
| 4,715,854 | 12/1987 | Vaillancourt . |
| 4,765,549 | 8/1988 | Sherman . |
| 5,118,021 | 6/1992 | Fiocchi . |

OTHER PUBLICATIONS

American Medical Industries brochure entitled "Making Your Medications & Vitamins EZ to Swallow", including enclosure entitled Remembering Your Medication Schedule is EZ.
American Medical Industries sales flier entitled "Welcome to American Medical Industries" Family of EZ–Health™ Products, 1993.
American Medical Industries Facsimile transmission to Lake Medical Products regarding EZ–Swallow Pill Crushers & Pill Splitters, Sep. 1, 1993.
Gerber Products Company, Baby Medi–Spoon, 1991.

*Primary Examiner*—C. Fred Rosenbaum
*Assistant Examiner*—Perry E. Van Over
*Attorney, Agent, or Firm*—Rogers, Howell & Haferkamp

[57] ABSTRACT

A pill crushing/dispensing device includes a plunger having a handle at one end and an abraded surface at the other, and a barrel/spoon unit which has an opposing abraded surface in its bottom interior so that a pill is crushed between the abraded surfaces as the plunger is advanced into the barrel. After the pill is crushed between the abraded surfaces, the plunger is removed and a fluid added to create a suspension of pill crushings which may then be orally administered by tipping the barrel/spoon unit to a generally horizontal position so that the fluid flows into the spoon unit which may then itself be inserted into a patient's mouth. In alternative embodiments, a central air passageway extends the length of the plunger unit to facilitate the flow of air to and from an air pocket between the abraded surfaces to facilitate the easy movement of the plunger within the closed barrel. A cap may be used to selectively seal the passageway. In an alternative construction, the plunger may be hollow to contain additional pills for later administration, and a cap provided to seal the hollow interior of the plunger and retain the pills therein.

15 Claims, 1 Drawing Sheet

HAND HELD COMBINATION PILL CRUSHING AND DISPENSING DEVICE

This is a continuation-in-part of application Ser. No. 08/168,019; filed on Dec. 15, 1993, now U.S. Pat. 5,376, 072.

CROSS-REFERENCE TO RELATED APPLICATION

This application is a continuation-in-part of Ser. No. 08/168,019, filed Dec. 15, 1993.

BACKGROUND AND SUMMARY OF THE INVENTION

Administering medicine, vitamins, or other pills to infants can be difficult at best. As a consequence, many medicines such as aspirin, antibiotics, and other drugs are made and sold in liquid form for easy administration to small children and infants. For those instances where the medicine is not available in liquid form, and perhaps only in tablet form, a pill must be separately crushed with, for example, a mortar and pestle, and the powder or pill crushings transferred to another container or dispensing utensil where it can be mixed with fluid for oral administering of the drug to the patient. There are several drawbacks with this technique, as pointed out in the parent hereof, such as the risk of low and unpredictable compliance and cross contamination. As disclosed and claimed in the parent, the disclosure of which is incorporated herein by reference, this same problem exists for many infirm adult patients and the solution thereto was provided by the pill crushing syringe disclosed and claimed in the parent. However, there are many occasions when it is not desired to administer the medicine through a syringe and instead it is desired to be orally administered.

In order to solve these and other problems in the prior art, and as an extension of the general concept disclosed and claimed in the parent, the inventor herein has succeeded in designing and developing a hand held pill crushing and dispensing device for the oral administering of medicine to infants and others to whom for whatever reason it is desirable to orally administer medicine but are unable to swallow a pill. In its simplest form, the present invention includes a container in the form of a barrel with an abraded surface on its bottom interior surface with a removable plunger having a matching abraded surface for insertion therein to crush a pill. A dispensing utensil, such as a spoon or the like, extends from the lip of the barrel, and may be integrally formed therein during manufacturing, so that the pill crushings may be mixed with a fluid and poured into the spoon for oral administration all in the same hand held device.

As the barrel has a closed end, unlike the pill crushing syringe disclosed in the parent hereof, one of several constructions may be used to facilitate the advancing of the plunger into the barrel closed end which is otherwise resisted by the pocket of air trapped between the plunger and barrel. One such solution is to provide a sufficient tolerance between the plunger and barrel sidewall so that the pocket of air may escape through the space therebetween as the plunger is advanced. Still another solution is to provide an air passageway through the length of the plunger which may be sealed at its outer end to allow for the fluid/pill crushing mixture to be shaken and yet prevent any escape thereof through the passageway. Alternately, a cork or other closure may be directly inserted into the barrel to close it off after fluid has been added to agitate the fluid/pill crushings into a suspension for administration.

Still other variations of construction include a threaded fitting between the plunger and barrel which provide for a positive advancement of the plunger within the barrel by a twisting of the plunger with respect to the barrel to thereby allow for greater force to be applied in crushing a pill. In still another alternative construction, the lunger may itself be hollow and a cap be provided to enclose the plunger and provide a ready container for storage of additional tablets of medicine for later administration.

As explained above, one of the useful features of the present invention is the integral formation of a spoon to the lip of the barrel into which the suspension may be poured by merely tilting the barrel into a generally horizontal orientation. This eliminates any transfer of pill crushings from one container to another which could result in low or unpredictable compliance and the risk of cross contamination as is prevalent with prior art devices. Furthermore, a parent may confidently bring the pill crushing device close to the mouth of a flailing infant in a vertical orientation and avoid the significant risk of spilling the medicine which is inherent with a typical spoon type administration technique. Upon readying the infant for administration of the medicine, the pill crushing device may then be quickly reoriented from vertical to horizontal and, if desired, in one quick motion inserted into the infant's mouth to orally administer the medication.

The elegantly simple design of the present invention facilitates its manufacture through high speed low cost plastic manufacturing processes to permit their economical production and sale at low cost for single use application. Alternately, other constructions could be utilized to provide multiple use devices which are suitable for repeated cleaning or sterilization, as appropriate. Thus, with the present invention, a hand held device to crush a pill and orally administer its crushings as a suspension in a fluid may be widely used in an economical and cost effective manner to satisfy a long felt need.

While the principal advantages and features of the present invention have been briefly described above, a more thorough understanding and appreciation for the invention's advantages and features may be attained by referring to the drawings and description of the preferred embodiment which follow.

DETAILED DESCRIPTION OF THE PREFERRED EMBODIMENT

Figure 1:
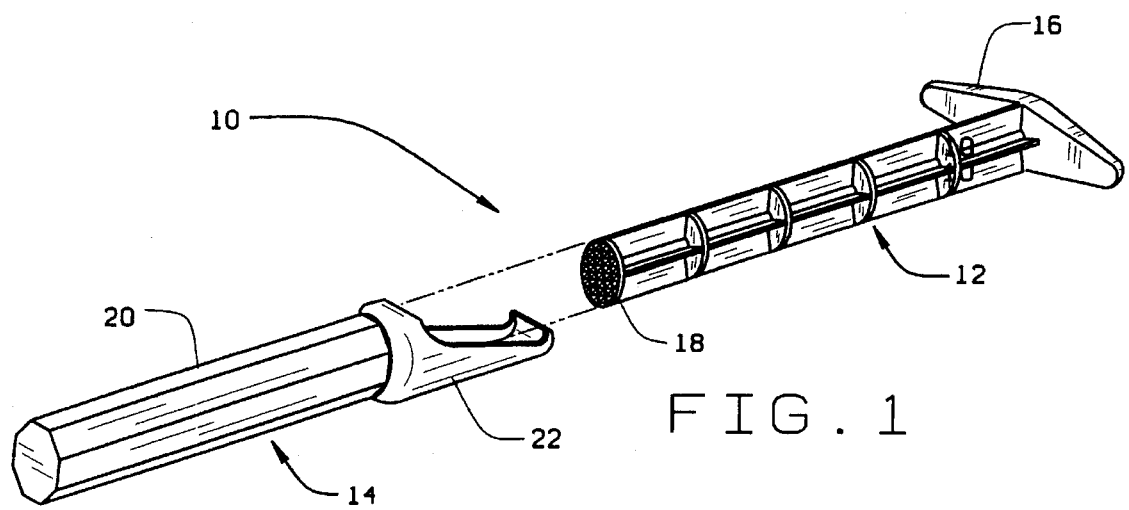
FIG. 1 is a perspective view of the pill crushing/dispensing device of the present invention showing the removable plunger and barrel/spoon elements.

The pill crushing/dispensing device 10 of the present invention includes a removable plunger 12, and a barrel/spoon unit 14. The plunger 12 has a handle 16 at one end thereof and an abraded surface 18 at its tip end. The barrel/spoon nit 14 is comprised of a barrel 20 and an integrally formed spoon 22. Alternately, the spoon 22 may be separately made and attached for use. Not shown in FIG. 1 is an abraded surface which is in the bottom interior of barrel 20 which is in opposition to and lines up with abraded surface 18 of plunger 12 as it is advanced therein.

Figures 2, 3:
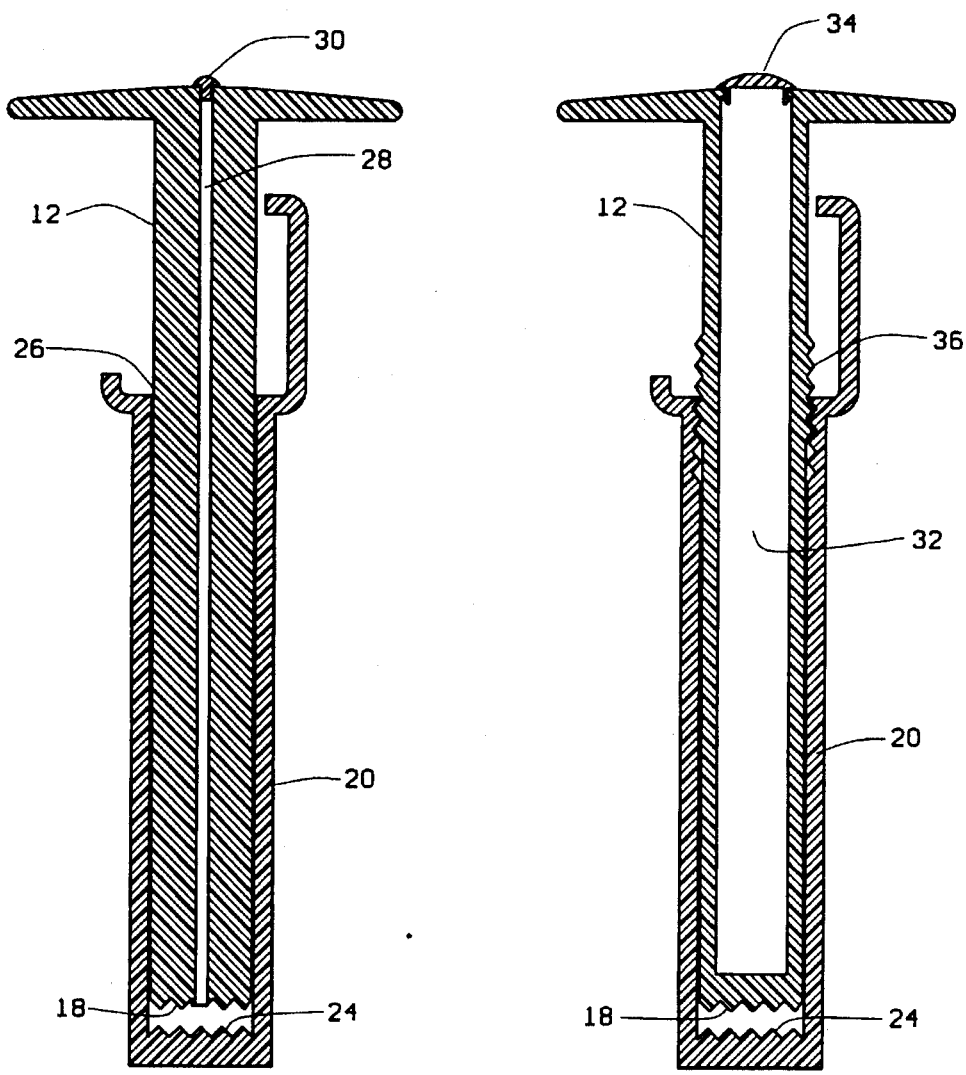
FIG. 2 is a cross-sectional view of the pill crushing/dispensing device of the present invention with the plunger inserted in the barrel, and further detailing a central air passageway with cap sealer.
FIG. 3 is a cross-sectional view of the pill crushing/dispensing device of the present invention with a plunger of an alternative embodiment having a capped opening for storing additional pills.

Referring to FIG. 2, the barrel abraded surface 24 is depicted as described above in matched opposition to the plunger abraded surface 18. These abraded surfaces 18, 24 are brought together as the plunger 12 is advanced within the barrel 20. To avoid a pocket of air from forming in the space between abraded surfaces 18, 24, either one of two constructions may be used. Plunger 12 may have an outside diameter which provides a gap 26 between it and the inner sidewall of barrel 20. This gap 26 provides an avenue for air to be pushed out of the pocket between abraded surfaces 18, 24 as the plunger 12 is advanced into the barrel 20. With this construction, fluid poured into the barrel after the pill is crushed may undesirably migrate up the gap 26 and take with it some of the pill crushings as the pill crushing/dispensing device 10 is vibrated or agitated during the mixing step. This may or may not present a problem depending upon the vibrating action chosen by the user, the size of the gap 26, the nature or size of the pill crushings, and other variables. Thus, this construction may very well be appropriate and successful for some or all applications.

Alternatively, an air passageway 28 may extend the length of plunger 12 and a cap 30 used to seal passageway 28, when desired. Cap 30 is removed when it is desired to move plunger 12 into or out of barrel 20 as it provides a ready avenue for the passage of air into or out of the air pocket between abraded surfaces 18, 24. However, during the mixing step, cap 30 may replaced to resist migration of the pill crushings suspension through air passageway 28. With this alternative construction, a much closer tolerance may be held between the outside diameter of plunger 12 and the inside diameter of barrel 20.

As shown in FIG. 3, still another alternative construction is shown wherein the plunger 12 has a hollow interior 32 which is sealed by a cap 34. The hollow interior 32 may be conveniently used to store additional pills so that they are at hand when it is desired to crush and administer medicine with the pill crushing/dispensing device of the present invention. Also shown in FIG. 3 is a threaded fitting 36 which joins the plunger 12 to barrel 20 so that twisting of the plunger 12 with respect to the barrel unit 20 serves to positively advance the plunger 12 and bring abraded surfaces 18, 24 together under much greater pressure. This helps achieve a more thorough crushing of a pill.

In its use, the pill crushing/dispensing device of the present invention is elegantly simple and provides significant advantages over the prior art. The method of using the pill crushing/dispensing device of the present invention is also novel and unique and includes the steps of placing a pill in the barrel, advancing the plunger in the barrel to crush the pill between the abraded surfaces, withdrawing the plunger from within the barrel and adding a suitable dispensing fluid such as distilled water or the like, closing the barrel by either reinserting the plunger or with a temporary closure such as a cork, cap, or other suitable device, vibrating the pill crushing/dispensing device to agitate the fluid/pill crushings suspension which serves to effectively dislodge pill crushings from one or both abraded surfaces, removing the temporary closure, and administering the fluid/pill crushings suspension by tilting the barrel/spoon unit to a generally horizontal orientation for insertion into an infant's mouth. Alternate steps may also be performed as part of the method including twisting the plunger within the barrel to positively advance the plunger in the barrel with the threaded fitting, appropriately opening and closing the air passageway with its associated cap to facilitate advancing and withdrawing the plunger within the barrel/spoon unit, and twisting the plunger within the barrel/spoon unit to more completely grind the capsule between the abraded surfaces.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A hand held, combination pill crushing and dispensing device comprising a container, means for crushing a pill placed within said container, and a dispensing spoon extending from said container so that a pill crushed within said container may be mixed with a dispensing fluid and directly dispensed with said dispensing spoon to a patient as it flows out of said container.

2. The device of claim 1 wherein said pill crushing means comprises a plunger for insertion into said container.

3. The device of claim 2 wherein said pill crushing means includes at least one abraded surface.

4. The device of claim 3 wherein said pill crushing means includes a pair of opposing abraded surfaces, one on each of said container and said plunger, so that a pill placed between said abraded surfaces may be crushed therebetween as said plunger is advanced into said container.

5. The device of claim 4 further comprising means for controllably advancing said plunger within said container.

6. The device of claim 5 wherein said advancing means comprises a threaded fitting between said plunger and container.

7. The device of claim 5 wherein said container is a barrel, said abraded surface is at the bottom of said barrel and said other abraded surface is at a tip end of said plunger so that as said plunger bottoms in said barrel said abraded surfaces contact each other and crush any pill placed therebetween.

8. A hand held, combination pill crushing and dispensing device comprising a barrel having an abraded surface in its bottom, a plunger having an abraded surface at its tip end so that as said plunger is advanced to the barrel bottom the two abraded surfaces contact each other and crush any pill placed therein, and a dispensing spoon integrally formed at the top of said barrel so that any fluid mixed with a pill crushed in said barrel will flow into said spoon for dispensing as said barrel is tipped into a generally horizontal orientation.

9. The device of claim 8 further comprising a threaded fitting between said barrel and plunger to thereby positively advance said plunger within said barrel and facilitate the crushing of a pill.

10. The device of claim 8 further comprising an air passage through said plunger to thereby facilitate the insertion of said plunger into said barrel.

11. The device of claim 10 further comprising means for sealing said air passage to thereby facilitate the sealing off of said barrel and any fluid contained therein for mixing with said pill crushings.

12. A method of crushing and dispensing a pill suspended in a fluid with a hand held pill crushing and dispensing device comprising the steps of:

placing a pill into a container in the device;

crushing the pill by advancing a plunger into the container;

mixing the pill crushings with a fluid added to the container; and directly dispensing the fluid mixture through a dispensing spoon extending from said container.

13. The method of claim 12 wherein the step of crushing the pill includes the step of positively advancing the plunger into the container by turning the plunger with respect to the container to thereby engage a threaded fitting therebetween.

14. The method of claim 12 wherein the step of mixing includes the steps of removing the plunger from the container prior to the adding of fluid, reinserting the plunger in the container to thereby seal the container, and vibrating the container to agitate the fluid suspension.

15. The method of claim 14 wherein the step of reinserting the plunger includes the step of sealing off an air passage through said plunger prior to vibrating the container.

* * * * *